US005082961A

United States Patent [19]

Fukumoto et al.

[11] Patent Number: 5,082,961

[45] Date of Patent: Jan. 21, 1992

[54] METHOD FOR THE PREPARATION OF AN ALKYNYL COMPOUND

[75] Inventors: Takehiko Fukumoto; Akira Yamamoto, both of Niigata, Japan

[73] Assignee: Shin-Etsu Chemical Co., Ltd., Tokyo, Japan

[21] Appl. No.: 580,789

[22] Filed: Sep. 11, 1990

[30] Foreign Application Priority Data

Sep. 19, 1989 [JP] Japan .................................. 1-243021

[51] Int. Cl.$^5$ ........................... C07F 7/08; C07C 2/02

[52] U.S. Cl. .................................... 556/466; 585/505; 585/534

[58] Field of Search ................. 556/466; 585/505, 534

[56] References Cited

U.S. PATENT DOCUMENTS 2,855,441 10/1919 Sondheimer ........................ 260/615
4,384,158 5/1983 Ishihara et al. ..................... 585/534

*Primary Examiner*—JoséG. Dees
*Assistant Examiner*—Porfirio Nazario
*Attorney, Agent, or Firm*—Wyatt, Gerber, Burke & Badie

[57] ABSTRACT

A novel and efficient method is proposed for the synthetic preparation of a long-chain alkynyl compound in a one-pot reaction without isolating the intermediate from the reaction mixture. The inventive method comprises the steps of: (a) a Grignard coupling reaction of an ω-halogeno-1-alkynyl magnesium halide compound of the general formula $X^1MgC \equiv C(CH_2)_nX^2$, in which $X^1$ is a halogen atom, $X^2$ is an atom of Br or I and n is 3 to 10, and a Grignard reagent of the general formula $RMgX^1$, in which R is a group selected from the class consisting of alkyl groups, alkenyl groups, alkynyl groups, alkapolyenyl groups, aryl groups and hydrocarbon groups having protected hydroxy group to give an intermediate compound of the general formula $X^1MgC \equiv C(CH_2)_nR$; (b) subjecting the intermediate compound to a reaction with a reactant selected from the class consisting of $C_2$-synthons, $C_1$-synthons and chlorosilane compounds having reactivity with the intermediate compound at the $X^1Mg$-terminal; and (c) hydrolyzing the reaction product obtained in step (b).

4 Claims, No Drawings

METHOD FOR THE PREPARATION OF AN ALKYNYL COMPOUND

BACKGROUND OF THE INVENTION

The present invention relates to a novel method for the preparation of an alkynyl compound. More particularly, the invention relates to a novel synthetic method for the preparation of various kinds of alkynyl compounds useful as an intermediate of various organic compounds used as agricultural chemicals or, in particular, sex pheromones of insect pests, in which the desired alkynyl compound can be obtained without isolating the intermediate product in the successive steps of reactions.

In the prior art, a long-chain alkynyl compound is usually synthesized by a method in which the chain length of the alkynyl group of the starting alkynyl compound is extended by adding a chain segment of a desired length to each side of the triple bond separately from the other side. This conventional method, however, has a disadvantage that the yield of the desired compound cannot be high enough for the reasons that the synthetic process is lengthy and complicated because the chain extension must be undertaken separately at both sides of the triple bond of the starting alkynyl compound, that the functional groups must be protected by a protective group which must be subsequently eliminated, that the reaction sometimes must be performed at a high temperature under a superatmospheric pressure or at a low temperature in order to impart the reactive site of the starting compound with selectivity for the desired reaction and so on.

For example, Japanese Patent Kokai 57-24392 teaches a method for the synthesis of cis-13-octadecen-3-yn-1-ol of the formula $HO(CH_2)_2C{\equiv}C(CH_2)_6R$, in which R is cis-3-octenyl group, as an intermediate for the synthesis of the sex pheromone of a notorious pest *Synanthedon hector*. The synthetic method thereof is a two-step process consisting of the first reaction of 8-bromo-1-octyne with cis-3-octenyl magnesium chloride to form cis-11-hexadecen-1-yne of the formula $HC{\equiv}C(CH_2)_6R$, which is then reacted in the second step reaction with methyl magnesium chloride and ethylene oxide to give the desired product. The reactions must be conducted at a low temperature and the overall yield of the desired product is not high enough with the partial yields in the first step and second step reactions of 60% and 90%, respectively.

Thus, it is eagerly desired to develop an efficient method for the synthetic preparation of a long-chain alkynyl compound in a relatively simple process which can be performed without chilling the reaction mixture or requiring other special reaction conditions but still give the desired product in a high yield.

SUMMARY OF THE INVENTION

The present invention accordingly has an object to provide a novel and efficient method for the synthetic preparation of a long-chain alkynyl compound from a starting compound having a shorter chain length than in the alkynyl group of the desired product compound.

Thus, the method of the present invention for the preparation of a long-chain alkynyl compound comprises the steps of:

(a) subjecting an ω-halogeno-1-alkynyl magnesium halide compound represented by the general formula $$X^1MgC{\equiv}C(CH_2)_nX^2, \quad (I)$$

in which $X^1$ is a halogen atom, $X^2$ is an atom of bromine or iodine and the subscript n is an integer in the range from 3 to 10, and an unsubstituted or substituted Grignard reagent represented by the general formula $$RMgX^1, \quad (II)$$

in which $X^1$ has the same meaning as defined above and R is a group selected from the class consisting of alkyl groups, alkenyl groups, alkynyl groups, alkapolyenyl groups, aryl groups and hydrocarbon groups having a protected hydroxy group, to a Grignard-coupling reaction to give an intermediate compound represented by the general formula $$X^1MgC{\equiv}C(CH_2)_nR, \quad (III)$$

in which each symbol has the same meaning as defined above;

(b) subjecting the intermediate compound to a reaction with a reactant selected from the class consisting of $C_2$-synthons, $C_1$-synthons and chlorosilane compounds having reactivity with the intermediate compound at the $X^1Mg$-terminal; and (c) hydrolyzing the reaction product obtained in step (b).

In particular, the above mentioned $C_2$-synthon is preferably ethylene oxide and examples of the $C_1$-synthon include ethyl chlorocarbonate, methyl chlorocarbonate, carbon dioxide, ethyl orthoformate, methyl orthoformate and paraformaldehyde.

DETAILED DESCRIPTION OF THE PREFERRED EMBODIMENTS

As is described above, the inventive method for the synthesis of an alkynyl compound is a two-step process comprising the steps (a) and (b) followed by the hydrolysis reaction in step (c). Advantageously, however, the reaction of step (b) can be conducted without isolating the intermediate compound of the formula (III) from the reaction mixture of the step (a) reaction so that the process as a whole can be greatly simplified and the yield of the desired final product can be increased so much.

The reaction of step (a) is expressed by the reaction equation $$X^1MgC{\equiv}C(CH_2)_nX^2 + RMgX^1 \rightarrow X^1MgC{\equiv}C(CH_2)_nR + MgX^1X^2, \quad (IV)$$

in which each symbol has the same meaning as defined above. On the other hand, the reaction of step (b) is expressed either one of the following reaction equations depending on the type of the reactant:

$$X^1MgC{\equiv}C(CH_2)_nR + (C_2\text{-synthon}) \rightarrow C_2\text{-}C{\equiv}C(CH_2)_nR, \quad (V\text{-}1)$$

when the reactant is a $C_2$-synthon;

$$X^1MgC{\equiv}C(CH_2)_nR + (C_1\text{-synthon}) \rightarrow C_1\text{-}C{\equiv}C(CH_2)_nR, \quad (V\text{-}2)$$

when the reactant is a $C_1$-synthon; and $$X^1MgC{\equiv}C(CH_2)_nR + {\equiv}Si\text{-}Cl \rightarrow {\equiv}C(CH_2)_nR, \quad (V\text{-}3)$$

when the reactant is a chlorosilane compound.

The above described inventive method is particularly useful for the preparation of, for example, cis-13-octadecen-3-yn-1-ol as an intermediate compound in the synthesis of the sex pheromone compound of *Synanthedon hector* in respect of the mild reaction conditions requiring no particularly high or low temperatures and the high yield reaching about 70% or even higher. The procedure for the preparation of this cis-13-octadecen-3-yn-1-ol will be described later in detail by way of an example.

Thus, the inventive method is very advantageous for the synthetic preparation of a long-chain alkynyl compound in respect of (1) the mild reaction conditions requiring no particular equipment for the reaction, (2) the simplicity of the process because the intermediate compound formed in step (a) need not be isolated from the reaction mixture prior to step (b) so that the whole process can be conducted in a single reaction vessel and (3) the outstandingly high yield of the desired final product.

One of the starting materials in the reaction of step (a) is an ω-halogeno-1-alkynyl magnesium halide compound represented by the general formula (I) given above, in which $X^1$ is an atom of halogen including chlorine, bromine and iodine, $X^2$ is an atom of bromine or iodine and the subscript n is an integer of 3 to 10. This compound can be easily prepared by the reaction of an ω-halogeno-1-alkyne compound of the formula $HC \equiv C(CH_2)_nX^2$ with methyl magnesium chloride or ethyl mangnesium bromide. A number of compounds can be named as the particular examples of the ω-halogeno-1-alkynyl magnesium halide compound in conformity with the general formula (I) with variable combinations of the halogens denoted by $X^1$ and $X^2$ and the number of the subscript n including, for example, 5-bromo-1-pentynyl magnesium chloride of the formula $ClMgC \equiv C(CH_2)_3Br$, in which $X^1$ and $X^2$ are chlorine and bromine atoms, respectively, and n is 3 in the formula (I), 12-iodo-1-dodecynyl magnesium chloride of the formula $ClMgC \equiv C(CH_2)_{10}I$, in which $X^1$ and $X^2$ are chlorine and iodine atoms, respectively, and n is 10 in the formula (I), and the like.

In step (a) of the inventive method, the above described ω-halogeno-1-alkyne compound is subjected to a Grignard coupling reaction with a Grignard reagent represented by the general formula (II) given above, in which $X^1$ has the same meaning as defined above and R is an unsubstituted or substituted hydrocarbon group selected from the class consisting of alkyl groups, e.g., propyl, hexyl, octyl and isobutyl groups, alkenyl groups, e.g. cis-3-octenyl, cis-4-nonenyl and cis-4-octenyl groups, alkynyl groups, e.g., 7-decynyl and 7,9-dodecadiynyl groups, alkapolyenyl groups, e.g., cis-3-cis-6-nonadienyl, trans-7-cis-9-tridecadienyl and 3,5,7-undecatrienyl groups, aryl groups, e.g., phenyl group, aralkyl groups, e.g., benzyl group, and hydrocarbon groups having a protected hydroxy group, e.g., 6-(trimethylsiloxy)hexyl and 5-(tetrahydropyranyloxy)-pentyl groups.

The Grignard coupling reaction of step (a) in the inventive method is performed by dissolving the ω-halogeno-1-alkynyl magnesium halide compound of the general formula (I) in an organic solvent such as tetrahydrofuran, diethyl ether, dibutyl ether, dioxane, toluene and the like or a mixture thereof with admixture of a copper compound as a catalyst such as copper (I) compounds, e.g., copper (I) iodide, copper (I) chloride and the like, copper (II) compounds, e.g., copper (II) chloride, copper (II) acetate and the like, as well as complexes of copper with lithium, e.g., $Li_2CuCl_4$, and adding the Grignard reagent of the general formula (II) in an amount of 1.0 to 1.2 moles per mole of the ω-halogeno-1-alkynyl magnesium halide compound. A preferable organic solvent is tetrahydrofuran which is used in an amount of 300 to 600 g per mole of the ω-halogeno-1-alkynyl magnesium halide compound. The amount of the copper catalyst is usually in the range from 0.01 to 0.07 mole per mole of the ω-halogeno-1-alkynyl magnesium halide compound. Addition of a small amount of HMPA, triethyl phosphite, N,N-dimethyl formamide and the like is sometimes effective to promote the reaction. The reaction temperature is usually in the range from 10° to 70° C. or, preferably, from 30° to 60° C., at which the reaction is complete, usually, within 1 to 5 hours or, in most cases, within 2 to 4 hours. The end point of the reaction can be determined by the gas chromatographic analysis of the reaction mixture.

The product formed by the reaction of step (a) in the inventive method is also a Grignard compound represented by the general formula (III) given above. This compound, having a halogenomagnesium group $X^1Mg$- at the molecular chain end, is also capable of pertaining to a reaction characteristic to a Grignard compound with various reactants giving a possibility of introducing a second chain-extending segment at the other side of the triple bond of the starting ω-halogeno-1-alkynyl magnesium halide compound than the side to which a first chain-extending segment has been introduced in the reaction of step (a). This is the reaction in step (b) of the inventive method.

The reactants used in the reaction of step (b) can be categorized into three classes including the $C_2$-synthon compounds, $C_1$-synthon compounds and chlorosilane compounds. A typical example of the $C_2$-synthon compound is ethylene oxide while preferable examples of the $C_1$-synthon compound include ethyl chlorocarbonate, methyl chlorocarbonate, carbon dioxide, ethyl orthoformate, methyl orthoformate and paraformaldehyde. The chlorosilane compound is exemplified by trimethyl chlorosilane, dimethyl dichlorosilane, methyl trichlorosilane, dimethyl chlorosilane and the like though not particularly limitative thereto.

The exact reaction conditions in step (b) naturally depend on the types of the above described reactants to give a reaction product which also differs depending on the reactant. Following are the typical but non-limitative reaction conditions and the chemical formula of the reaction product after hydrolysis for each reactant.

i) Ethylene oxide

This reactant is used in an amount of 1.0 to 2.0 moles per mole of the intermediate of the general formula (III) and the reaction is performed at 10° to 50° C., at which the reaction is complete within 1 to 4 hours to give a product of the formula $HO(CH_2)_2C \equiv C(CH_2)_nR$.

ii) Paraformaldehyde

This reactant is used in an amount of 1.0 to 2.0 moles calculated as $CH_2O$ per mole of the intermediate of the general formula (III) and the reaction is performed at 60° to 75° C., at which the reaction is complete within 1 to 4 hours to give a product of the formula $HOCH_2C \equiv C(CH_2)_nR$.

iii) Ethyl and methyl chlorocarbonates

These reactans are used in an amount of 0.8 to 1.2 moles per mole of the intermediate of the general formula (III) and the reaction is performed at −20° to +30° C., at which the reaction is complete within 1 to 2 hours to give a product of the formula $C_2H_5OCOC\equiv C(CH_2)_nR$ and $CH_3OCOC\equiv C(CH_2)_nR$, respectively.

iv) Carbon dioxide

This reactant is used in an amount of 1.0 to 5.0 moles per mole of the intermediate of the general formula (III) and the reaction is performed at −20° to +30° C., at which the reaction is complete within 1 to 4 hours to give a product of the formula $HOCOC\equiv C(CH_2)_nR$.

v) Ethyl and methyl orthoformates

These reactans are used in an amount of 1.0 to 1.5 moles per mole of the intermediate of the general formula (III) and the reaction is performed at 75° to 100° C., at which the reaction is complete within 3 to 8 hours to give a product of the formula $(C_2H_5O)_2HCC\equiv C(CH_2)_nR$ and $(CH_3O)_2HCC\equiv C(CH_2)_nR$, respectively.

vi) Chlorosilanes

Trimethyl chlorosilane, dimethyl dichlorosilane, methyl trichlorosilane and dimethyl chlorosilane are used each in an amount of 0.8 to 1.2 moles per mole of the intermediate of the general formula (III) and the reaction is performed at −40° to +40° C. or, preferably, −20° to +40° C. at which the reaction is complete within 1 to 2 hours to give a product of the formula $Me_3SiC\equiv C(CH_2)_nR$, $Me_2ClSiC\equiv C(CH_2)_nR$, $MeCl_2SiC\equiv C(CH_2)_nR$ and $Me_2HSiC\equiv C(CH_2)_nR$, respectively, in which Me denotes a methyl group.

The above described method of the present invention is successfully applicable to the preparation of cis-3-cis-13-octadecadienyl acetate and trans-2-cis-13-octadecadienyl acetate, which are the sex pheromone compounds of the insects belonging to the order of Lepidoptera such as *Synanthedon exitiosa* and *Synanthedon tipuliformis*, respectively. Detailed synthetic conditions of these sex pheromone compounds will be described later by way of examples.

In the following, examples are given to illustrate the method of the invention in more detail but not to limit the scope of the invention in any way. Each of the reactions described below was conducted in an inert atmosphere of nitrogen or argon gas.

EXAMPLE 1 cis-13-Octadecen-3-yn-2-ol was synthesized in the following manner. Thus, a Grignard mixture containing 1.0 mole of methyl magnesium chloride dissolved in 300 ml of tetrahydrofuran was added dropwise into 153 g (0.81 mole) of 8-bromo-1-octyne kept at 50° to 55° C. and the reaction mixture was agitated for 1 hour at 60° C. followed by the addition of 2 g of copper (I) iodide CuI. Thereafter, a second Grignard mixture containing 1.0 mole of cis-3-octenyl magnesium chloride dissolved in 300 ml of tetrahydrofuran was added dropwise to the reaction mixture kept at 40° to 55° C. and the reaction mixture was agitated for 4 hours at 40° C.

Then, 88 g (2.0 moles) of ethylene oxide were added dropwise to the above obtained reaction mixture kept at a temperature of 40° C. or below and the reaction mixture was agitated for further 2 hours. After completion of the reaction, the reaction mixture was subjected to hydrolysis with 300 ml of a 20% hydrochloric acid and the organic solution was taken by phase separation and distilled under reduced pressure to give 150 g of a product boiling at 177° to 180° C. under a pressure of 2 mmHg, which could be identified to be cis-13-octadecen-3-yn-1-ol. The above mentioned yield of the product corresponded to 70% of the theoretical value.

The above prepared cis-13-octadecen-3-yn-1-ol was used as an intermediate for the preparation of cis-3-cis-13-octadecadienyl acetate as the sex pheromone compound of *Synanthedon exitiosa*. Thus, 150 g of the cis-13-octadecen-3-yn-1-ol were taken in an autoclave together with 150 g of n-hexane and 2 g of a Lindlar catalyst and hydrogen gas was introduced into the autoclave under a pressure of 5 $kg/cm^2$ G at 40° C. to effect partial hydrogenation for 3 hours. When the starting compound had completely disappeared as indicated by the result of the gas chromatographic analysis, the reaction mixture was taken out of the autoclave and filtered to remove the catalyst. The filtrate and 150 g of pyridine were taken in a reaction vessel to which 62 g of acetic anhydride were added dropwise at a temperature of 50° to 60° C. followed by further continued agitation of the reaction mixture at 70° C. for 2 hours. thereafter, the reaction mixture was admixed with 200 ml of deionized water and subjected to phase separation to discard the aqueous phase. The organic solution thus obtained was washed with 200 ml of a 5% hydrochloric acid and distilled under reduced pressure to give 153 g of a fraction boiling at 175° to 180° C. under a pressure of 2 mmHg, which could be identified to be the desired cis-3-cis-13-octadecadienyl acetate.

EXAMPLE 2 cis-13-Octadecen-2-yn-1-ol was synthesized in the following manner. Thus, 153 g (0.81 mole) of 8-bromo-1-octyne were added dropwise at 50° to 55° C. to 1 mole of methyl magnesium chloride dissolved in 300 ml of tetrahydrofuran and the mixture was agitated for 1 hour followed by the addition of 2 g of dilithium tetrachlorocuprate $Li_2CuCl_4$. Thereafter, a solution of 1 mole of cis-4-nonenyl magnesium chloride dissolved in 300 ml of tetrahydrofuran was added dropwise to the reaction mixture at 40° to 55° C. and the mixture was agitated for 4 hours at 48° C.

In the next place, 40 g (1.33 moles calculated as $CH_2O$) of paraformaldehyde were added to the reaction mixture which was agitated for 2 hours at 70° to 75° C. After completion of the reaction, the reaction product in the mixture was hydrolyzed by adding 300 ml of a 20% hydrochloric acid followed by phase separation to discard the aqueous phase. The organic solution thus obtained was washed with water and distilled under reduced pressure to give 146 g of cis-13-octadecen-2-yn-1-ol as a fraction boiling at 170° to 174° C. under a pressure of 1.5 mmHg. The yield corresponded to 68% of the theoretical value.

The above prepared cis-13-octadecen-2-yn-1-ol was used as an intermediate for the synthesis of trans-2-cis-13-octadecadienyl acetate as a sex pheromone compound of *Synanthedon tipliformis*. Thus, 15 g of cis-13-octadecen-2-yn-1-ol were taken in a reaction vessel together with 3 g (79 m moles) of lithium aluminum hydride and 100 ml of tetrahydrofuran and the mixture was agitated for 4 hours at 68° C. Thereafter, the reaction mixture was admixed with 3 ml of ethyl alcohol and the reaction product was hydrolyzed by the addition of 50 g of a 20% hydrochloric acid followed by phase separation to discard the aqueous phase. The thus obtained organic solution and 20 g of pyridine were taken in a reaction vessel to which 9 g of acetic anhydride were added dropwise at 40° to 50° C. followed by agitation for 2 hours at 70° C. The reaction mixture was then admixed with 50 ml of deionized water and subjected to phase separation to discard the aqueous phase. The thus obtained organic solution was washed with 50 ml of a 5% hydrochloric acid and distilled under reduced pressure to give 14 g of a fraction boiling at 175° to 180° C. under a pressure of 2 mmHg, which could be identified to be the desired trans-2-cis-13-octadecadienyl acetate.

EXAMPLE 3

Ethyl 2-hexadecynate was synthesized in the following manner. Thus, 220.5 g (0.9 mole) of 12-bromo-1-dodecyne were added dropwise to 1.0 mole of methyl magnesium chloride dissolved in 300 ml of tetrahydrofuran and the mixture was agitated for 1 hour at 50° to 55° C. followed by the addition of 2 g of copper (I) iodide CuI. Thereafter, 1.0 mole of propyl magnesium chloride dissolved in 400 ml of tetrahydrofuran was added to the mixture dropwise at 40° to 55° C. and the mixture was agitated for 4 hours at 40° C.

The reaction mixture was then admixed with 108.5 g (1.0 mole) of ethyl chlorocarbonate at 0° to 10° C. and agitated for 1 hour at 10° C. The reaction product in the mixture was hydrolyzed by the addition of 300 ml of a 20% hydrochloric acid followed by phase separation to discard the aqueous phase. The thus obtained organic solution was washed with water and distilled under reduced pressure to give 161 g of a fraction boiling at 130° to 132° C. under a pressure of 0.2 mmHg, which could be identified to be the desired ethyl 2-hexadecynate. The yield corresponded to 64% of the theoretical value.

The above prepared ethyl 2-hexadecynate was used as an intermediate for the synthetic preparation of trans-2-hexadecenoic acid as a constituent in the fatty acid of vegetable lipids. Thus, 5 g of the ethyl 2-hexadecynate and 0.2 g of a hydrogenation catalyst containing 5% of palladium on a carbon carrier were taken in an autoclave which was pressurized at 35° to 40° C. with hydrogen up to a pressure of 5 kg/cm$^2$ to effect partial hydrogenation for 4.5 hours. Thereafter, the reaction mixture was freed from the catalyst by filtration and heated at 100° C. for 20 hours under agitation together with 20 ml of a 20% aqueous solution of sodium hydroxide. The reaction mixture was then admixed with 50 ml of deionized water and subjected to extraction with 50 ml of diethyl ether. The extract was freed from the ether by evaporation and the residue was gas-chromatographically fractionated to give 2.1 g of trans-2-hexadecenoic acid as an acidic fraction.

EXAMPLE 4

Methyl 2-hexadecynate was synthesized in substantially the same manner as in the preparation of ethy 2-hexadecynate in the preceding example excepting replacement of 108.5 g of ethyl chlorocarbonate with 94.5 g (1.0 mole) of methyl chlorocarbonate to give 144 g of a fraction boiling at 128° to 133° C. under a pressure of 0.2 mmHg, which could be identified to be the desired methyl 2-hexadecynate. The yield of the product corresponded to 63% of the theoretical value.

EXAMPLE 5

2-Dodecyn-1-al diethyl acetal was synthesized in the following manner. Thus, 132 g (0.9 mole) of 5-bromo-1-pentyne were added dropwise at 50° to 55° C. to 1.0 mole of methyl magnesium chloride dissolved in 300 ml of tetrahydrofuran and the mixture was agitated for 1 hour at 60° C. followed by the addition of 2 g of copper (I) chloride CuCl. Thereafter, a solution of 1.0 mole of hexyl magnesium chloride in 300 ml of tetrahydrofuran was added dropwise at 45° to 55° C. to the reaction mixture which was agitated for 4 hours at 40° C.

In the nxt place, 148 g (1.0 mole) of ethyl orthoformate were added dropwise at 85° to 95° C. to the reaction mixture which was agitated for 10 hours at 95° C. followed by hydrolysis of the reaction product by the addition of 500 ml of a 5M aqueous solution of ammonium chloride and phase separation to discard the aqueous phase. The organic solution thus obtained was washed with water and distilled under reduced pressure to give 161 g of a fraction boiling at 153° to 158° C. under a pressure of 1 mmHg which could be identified to be the desired 2-dodecyn-1-al diethyl acetal. The yield of the product corresponded to 69% of the theoretical value.

EXAMPLE 6

Ethyl 10-hydroxy-2-decynate was synthesized in the following manner. Thus, 132 g (0.9 mole) of 5-bromo-1-pentyne were added dropwise at 50° to 55° C. to a solution of 1.0 mole of methyl magnesium chloride in 300 ml of tetrahydrofuran and the mixture was agitated for 1 hour at 60° C. followed by the addition of a solution of 1.0 g of lithium chloride LiCl and 1.5 g of copper (II) chloride $CuCl_2$ dissolved in 10 ml of tetrahydrofuran. Thereafter, a solution of 1.0 mole of 4-trimethylsilyloxy butyl magnesium chloride in 300 ml of tetrahydrofuran was added dropwise at 45° to 55° C. to the reaction mixture which was agitated fro 4 hours at 40° C.

In the next place, 108.5 g (1.0 mole) of ethyl chlorocarbonate were added dropwise at 10° to 20° C. to the reaction mixture which was agitated for 1 hour at 20° C. The reaction mixture was then admixed with 500 ml of a 5M aqueous solution of ammonium chloride to hydrolyze the reaction product followed by phase separation to discard the aqueous phase. The organic solution thus obtained was washed with water and subjected to purification by the column chromatography to give 129 g of a fraction which could be identified to be the desired ethyl 10-hydroxy-2-decynate. The yield of the product coresponded to 61% of the theoretical value.

The above prepared ethyl 10-hydroxy-2-decynate was used as an intermediate for the synthesis of 10-hydroxy-E-2-decenoic acid in the following manner. In the first place, a P-2Ni catalyst was prepared by dissolving 10 g of nickel acetate tetrahydrate in 250 ml of ethyl alcohol and adding 2.2 g of sodium borohydride to the solution. The nickel catalyst was introduced into an autoclave together with 129 g of the 10-hydroxyethyl-2-decynate and 2 g of ethylene diamine and the autoclave was pressurized with hydrogen up to a pressure of 5 kg/cm$^2$G at 30° to 40° C. The reaction mixture was freed from the ethyl alcohol by distillation and then from the catalyst by filtration and admixed with 40 g of sodium hydroxide followed by agitation for 7 hours at 80° to 90° C. The thus obtained oily matter was dissolved in ether and crystallized with hexane to give 71 g of a white crystalline product melting at 61° to 53° C., which could be identified to be the desired 10-hydroxy-E-2-decenoic acid by making comparison with an authentic sample.

EXAMPLE 7

1-Trimethylsilyl-1-tridecyne was synthesized in the following manner. Thus, 170 g (0.9 mole) of 8-bromo-1-octyne were added dropwise at 50° to 55° C. to a solution of 1.0 mole of methyl magnesium chloride in 300 ml of tetrahydrofuran and the mixture was agitated for 1 hour at 60° C. followed by the addition of 2 g of copper (I) iodide CuI. Further, a solution of 1.0 mole of n-pentyl magnesium bromide in 400 ml of tetrahydrofuran was added dropwise at 40° to 55° C. to the reaction mixture which was agitated for 4 hours at 40° C.

In the next place, 97 g (0.9 mole) of trimethyl chlorosilane were added dropwise at 0° to 20° C. to the reaction mixture which was agitated for 1 hour at 20° C. followed by the addition of 300 ml of a 20% hydrochloric acid to hydrolyze the reaction product and phase separation to discard the aqueous phase. The organic solution thus obtained was washed with water and distilled under reduced pressure to give 134 g of a fraction boiling at 128° to 140° C. under a pressure of 3 mmHg, which could be identified to be the desired 1-trimethylsilyl-1-tridecyne. The yield of the product corresponded to 59% of the theoretical value.

What is claimed is:

1. A method for the preparation of a long-chain alkynyl compound which comprises the steps of:

(a) subjecting an ω-halogeno1-alkynyl magnesium halide compound represented by the general formula $$X^1MgC \equiv C(CH_2)_nX^2,$$

in which $X^1$ is a halogen atom, $X^2$ is an atom of bromine or iodine and the subscript n is an integer in the range from 3 to 10, and an unsubstituted or substituted Grignard reagent represented by the general formula $$RMgX^1,$$

in which $X^1$ has the same meaning as defined above and R is a group selected from the class consisting of alkyl groups, alkenyl groups, alkynyl groups, alkapolyenyl groups, aryl groups and hydrocarbon groups having a protected hydroxy group, to a Grignard-coupling reaction to give an intermediate compound represented by the general formula $$X^1MgC \equiv C(CH_2)_nR,$$

in which each symbol has the same meaning as defined above;

(b) subjecting the intermediate compound to a reaction with a reactant selected from the class consisting of $C_2$-synthons, $C_1$-synthons and chlorosilane compounds having reactivity with the intermediate compound at the $X^1$Mg-terminal; and (c) hydrolyzing the reaction product obtained in step (b).

2. The method for the preparation of a long-chain alkynyl compound as claimed in claim 1 wherein the $C_2$-synthon is ethylene oxide.

3. The method for the preparation of a long-chain alkynyl compound as claimed in claim 1 wherein the $C_1$-synthon is selected from the class consisting of ethyl chlorocarbonate, methyl chlorocarbonate, carbon dioxide, ethyl orthoformate, methyl orthoformate and paraformaldehyde.

4. The method for the preparation of a long-chain alkynyl compound as claimed in claim 1 wherein the reaction of step (b) is performed without isolating the intermediate compound formed in step (a) from the reaction mixture.

* * * * *